(12) United States Patent
Peluso et al.

(10) Patent No.: US 11,399,739 B2
(45) Date of Patent: Aug. 2, 2022

(54) DEVICES, SYSTEMS AND METHODS FOR CONTEXTUALIZED RECORDING OF BIOMETRIC MEASUREMENTS

(71) Applicant: QARDIO, INC., San Francisco, CA (US)

(72) Inventors: Marco Peluso, London (GB); Rosario Iannella, Amsterdam (NL)

(73) Assignee: QARDIO, INC., San Francisco, CA (US)

( * ) Notice: Subject to any disclaimer, the term of this patent is extended or adjusted under 35 U.S.C. 154(b) by 38 days.

(21) Appl. No.: 16/422,169

(22) Filed: May 24, 2019

(65) Prior Publication Data

US 2019/0274593 A1 Sep. 12, 2019

Related U.S. Application Data

(63) Continuation of application No. 14/932,273, filed on Nov. 4, 2015, now abandoned.
(Continued)

(51) Int. Cl.
| | |
|---|---|
| *A61B 5/11* | (2006.01) |
| *A61B 5/022* | (2006.01) |
| *A61B 5/00* | (2006.01) |
| *A61B 5/0245* | (2006.01) |
| *A61B 5/0205* | (2006.01) |

(Continued)

(52) U.S. Cl.
CPC .......... *A61B 5/1112* (2013.01); *A61B 5/0205* (2013.01); *A61B 5/0245* (2013.01); *A61B 5/02233* (2013.01); *A61B 5/333* (2021.01); *A61B 5/7246* (2013.01); *A61B 5/0235* (2013.01); *A61B 5/1116* (2013.01); *A61B 5/14551* (2013.01); *A61B 5/443* (2013.01);
(Continued)

(58) Field of Classification Search
CPC ..... A61B 5/0261; A61B 5/0295; A61B 5/443; A61B 5/1112; A61B 5/0006; A61B 5/681; A61B 5/6823; A61B 5/6824; A61B 2560/0242; A61B 2560/0252; A61B 2560/0257; A61B 2560/0271
See application file for complete search history.

(56) References Cited

U.S. PATENT DOCUMENTS 4,353,374 A * 10/1982 Rebbe ................ A61B 5/02233
600/499
4,776,344 A 10/1988 Shirasaki et al.
(Continued)

FOREIGN PATENT DOCUMENTS

| CN | 107106057 A | 8/2017 |
|---|---|---|
| EP | 3024382 B1 | 7/2020 |

(Continued)

*Primary Examiner* — Nathan J Jenness
(74) *Attorney, Agent, or Firm* — Buchalter; Cecily Anne O'Regan (57) ABSTRACT

Described are apparatuses (e.g., devices, systems, software), and methods for monitoring the cardiac health of a patient which incorporates secondary information. The apparatus may be a heart rate monitor, a blood pressure monitor, an ECG or other biometric device in communication with an electronic device having communication ability. The devices detect a cardiac or other biometric measurement and correlate the detected information with secondary information, such as GPS data, to produce a contextualized measurement.

11 Claims, 9 Drawing Sheets

Related U.S. Application Data (60) Provisional application No. 62/075,445, filed on Nov. 5, 2014.

(51) Int. Cl.
  *A61B 5/333* (2021.01)
  *A61B 5/0235* (2006.01)
  *A61B 5/1455* (2006.01)

(52) U.S. Cl.
  CPC ............... *A61B 2560/0257* (2013.01); *A61B 2562/0204* (2013.01); *A61B 2562/0271* (2013.01)

(56) References Cited

U.S. PATENT DOCUMENTS

| | | |
|---|---|---|
| 4,911,169 A | 3/1990 | Ferrari |
| 5,025,791 A | 6/1991 | Niwa |
| D324,570 S | 3/1992 | Arioka et al. |
| D341,659 S | 11/1993 | Homayoun et al. |
| D349,575 S | 8/1994 | Columbo |
| D356,377 S | 3/1995 | Tsubota et al. |
| D373,419 S | 9/1996 | Muramatsu et al. |
| 5,595,180 A | 1/1997 | Ogura et al. |
| 5,687,732 A | 11/1997 | Inagaki et al. |
| 5,807,266 A | 9/1998 | Itonaga et al. |
| 5,885,220 A | 3/1999 | Schaer |
| 6,251,080 B1 | 6/2001 | Henkin et al. |
| 6,272,365 B1 | 8/2001 | Ronkainen et al. |
| 6,456,872 B1 * | 9/2002 | Faisandier ......... A61B 5/04085 600/390 |
| 7,122,009 B2 | 10/2006 | Fumuro et al. |
| 7,206,630 B1 * | 4/2007 | Tarler ............... A61B 5/6833 600/509 |
| D550,844 S | 9/2007 | Gutmann et al. |
| D582,043 S | 12/2008 | Koike et al. |
| D583,477 S | 12/2008 | Kato |
| D589,150 S | 3/2009 | Kato |
| D595,858 S | 7/2009 | Kazel |
| D597,676 S | 8/2009 | Copeland et al. |
| D603,521 S | 11/2009 | Lindberg et al. |
| D619,256 S | 7/2010 | Brady et al. |
| 7,794,405 B2 | 9/2010 | Karo et al. |
| D639,955 S | 6/2011 | Riobo Aboy et al. |
| 8,147,417 B2 | 4/2012 | Gavriely |
| D667,127 S | 9/2012 | Lindberg et al. |
| D676,137 S | 2/2013 | Lindberg et al. |
| 8,509,882 B2 | 8/2013 | Albert et al. |
| 9,026,202 B2 | 5/2015 | Albert |
| 2003/0220575 A1 | 11/2003 | Fumuro et al. |
| 2005/0075577 A1 | 4/2005 | Chen |
| 2005/0182332 A1 | 8/2005 | Sano et al. |
| 2006/0009697 A1 | 1/2006 | Banet et al. |
| 2006/0111639 A1 | 5/2006 | Su |
| 2006/0122518 A1 | 6/2006 | Machit et al. |
| 2007/0055120 A1 | 3/2007 | Juan |
| 2007/0100213 A1 | 5/2007 | Dossas et al. |
| 2008/0146947 A1 | 6/2008 | Kojima et al. |
| 2008/0177159 A1 | 7/2008 | Gavriely |
| 2009/0118628 A1 * | 5/2009 | Zhou ................ A61B 5/1075 600/499 |
| 2009/0216134 A1 | 8/2009 | Hollinger et al. |
| 2009/0318818 A1 * | 12/2009 | Whitaker ........... A61B 5/0002 600/495 |
| 2010/0010356 A1 | 1/2010 | Chan et al. |
| 2010/0063365 A1 * | 3/2010 | Pisani ............... A61B 5/0002 600/301 |
| 2010/0076276 A1 | 3/2010 | Gilland |
| 2010/0106016 A1 | 4/2010 | Orbay et al. |
| 2010/0106029 A1 | 4/2010 | Fraden |
| 2010/0177182 A1 | 7/2010 | Kagenow et al. |
| 2011/0054330 A1 | 3/2011 | Pfeiffer et al. |
| 2011/0112412 A1 | 5/2011 | Sano et al. |
| 2011/0208015 A1 | 8/2011 | Welch et al. |
| 2011/0208068 A1 * | 8/2011 | Ariga ................ A61B 5/0225 600/490 |
| 2011/0245697 A1 | 10/2011 | Miettinen |
| 2012/0238890 A1 | 9/2012 | Baker et al. |
| 2012/0316794 A1 | 12/2012 | Goh et al. |
| 2013/0138000 A1 | 5/2013 | Kinoshita et al. |
| 2013/0211269 A1 | 8/2013 | Leschinsky |
| 2013/0326790 A1 * | 12/2013 | Cauwels ........... A61B 5/02233 2/170 |
| 2014/0187890 A1 * | 7/2014 | Mensinger ......... A61B 5/14532 600/365 |
| 2014/0206954 A1 | 7/2014 | Yuen et al. |
| 2014/0266780 A1 | 9/2014 | Rahman et al. |
| 2014/0371607 A1 | 12/2014 | Fitzsimons et al. |
| 2014/0378781 A1 | 12/2014 | Peluso et al. |
| 2016/0120445 A1 | 5/2016 | Peluso et al. |
| 2017/0238825 A9 | 8/2017 | Fitzsimons et al. |

FOREIGN PATENT DOCUMENTS

| | | |
|---|---|---|
| KR | 1020010044241 A | 6/2001 |
| KR | 1020120116331 A | 10/2012 |
| WO | 2004026126 A1 | 4/2004 |
| WO | 2011034881 A1 | 3/2011 |
| WO | 2014041363 A2 | 3/2014 |
| WO | 2014210127 A1 | 12/2014 |
| WO | 2016073692 A1 | 5/2016 |

* cited by examiner

TABLE 1
OPERATING PARAMETERS

| | |
|---|---|
| Patient/User Profile | Diagnostic (Dx) |
| | Clinical Profile |
| | Medication Requirements |
| Clinical Data | Diastolic Measurement |
| | Systolic Measurement |
| | Heart rate measurement |
| Location Data | GPS Location |
| | Altitude |
| Behavioral Data | Diet |
| | Exercise |

FIG. 5

DEVICES, SYSTEMS AND METHODS FOR CONTEXTUALIZED RECORDING OF BIOMETRIC MEASUREMENTS

CROSS-REFERENCE

This application is a continuation application of U.S. application Ser. No. 14/932,273 filed Nov. 4, 2015 which claims the benefit of U.S. Provisional Application No. 62/075,445, filed Nov. 5, 2014, which applications are incorporated herein by reference.

BACKGROUND

People are increasingly interested in technology that tracks health and wellness indicators into their daily routine. While the collection of wellness information has witnessed the integration of an increasing number of sensors, usually to infer things that are hard to measure directly, for example to collect light and noise information to supplement data on sleep quality, little or no progress has taken place for obtaining and managing a robust suite of medical data combined with data on the context before, during and after the medical data measurement is taking place. What is needed is a device or a combination of devices that collects medical data from a patient and correlates the data acquisition with other information, such as environmental information, to provide a contextualized profile for a particular user at a given time. This is increasingly important as modern technologies and modern lifestyles afford and/or require the measurement of biometrics with increasing frequency and across an increasing variety of times and places.

SUMMARY

Disclosed are devices, systems and methods that are configurable to automatically record a biometric measurement such as blood pressure and/or other biometric health related data together with geo-location or other contextual or environmental data, using coordinates from global positioning system ("GPS") signals and/or other contextual sensors, like accelerometers (for movement detection), barometers, thermometers (for both environmental and body temperature measurement). Other sensors include, for example, UV exposure, noise (from a microphone), galvanic skin response, body posture, and skin hydration. Automatically recorded data is stored locally and/or in a remote centralized location and can be retrieved by a user, or other person with the right to access the data, at any time for analysis, or can be used by the system to aid the user in capturing more effectively or more reliably the biometric measurements. Capturing blood pressure and location data simultaneously, for example, can help users identify trends, for example related to stress or inactivity, or help identify external factors affecting negatively the user's health. In another application, information on the user's activity, speed or location can be used by the system to prompt the user with a notification to perform a biometric measurement or to instead delay such notification until the user finds itself in a context more suitable to the biometric measurement. In another application the geolocation of electrocardiograph ("ECG") data and a secondary data such as respiratory rate data or blood pressure, could facilitate the identification that certain blood pressure problems or ECG anomalies occur, for example, at high altitudes. Another application could involve the combination of the prothrombin time ("PT") and its derived measures of prothrombin ratio ("PR") and international normalized ratio ("INR") (see, e.g., http://en.wikipedia.org/wiki/Prothrombin_time) tracking with weather data derived directly (e.g. from light sensors on the body of the user), or indirectly derived from weather reported at the geolocation of the user, to better monitor the effects of sunlight on the effectiveness/dosage of anticoagulants or other drugs.

An aspect of the disclosure is directed to an apparatus adapted to correlate a blood pressure measurement with GPS data or other contextual data before, during and/or after the measurement. Suitable apparatuses comprise: a cuff for wrapping around a limb of a subject the cuff further having a an inflatable bladder formed integrally therein, wherein the cuff is substantially rectangular in shape having a first surface, a second surface, a first end, a second end, and two sides, and a securement mechanism; one or more tubes positioned within the cuff in communication with the inflatable bladder; an exhaust valve; a displayless housing connected to one of a first end and a second end of the cuff wherein the housing includes one or more of a controller, a memory, a pump, a power supply, and a motor; a GPS sensor and/or other sensor or combination of sensors in communication with the apparatus; and a transmitter for wirelessly transmitting blood pressure data to a second device. Other sensors, can include accelerometers (for movement detection), barometers, thermometers (for both environmental and body temperature measurement), UV exposure, noise, galvanic skin response, body posture, and skin hydration. In some configurations, the blood pressure monitor device is configurable to be in communication with a communication network; and a computer executable instruction that, when executed by a processor analyzes a received blood pressure data and GPS data and/or other contextual sensor data. Additionally, the computer executable instructions can analyze one or more of patient data and electronic device data. In some configurations, the historical user data and historical GPS data is accessible via a communication network. One or more of an on-off button and a start-stop button can also be provided. Additionally, the device can comprise a pressure detector, and/or a pulse detector. Patient data and electronic device data can also be accessible via a communication network. Additionally, the blood pressure monitoring device is in wireless communication with one or more displays.

Another aspect of the disclosure is directed to a computing device comprising: a processor configured to: receive a GPS location, a historic patient data, and physiological cardiac condition indication for a user wherein the physiologic cardiac condition is selected from heart rate, blood pressure, and ECG; at least one or more of analyze, monitor, evaluate, and provide a prediction for a user based on the GPS location of the user and the physiological cardiac condition indication for the user. The computing devices can further have a processor that is configured to receive an input for stress level or activity level. Additionally, the processor can be configured to at least one or more of analyze and evaluate the historical patient data. In at least some configurations, the processor is capable of generating and delivering a blood pressure event message to one or more of the user, and a healthcare provider. Additionally, the processor can be associated with an electronic device and the electronic device is at least one of a blood pressure monitor and a mobile communication device. In still other configurations, the processor is in communication with one or more of the electronic device, a remote server, and the blood pressure monitor within near field communication range.

Yet another aspect of the disclosure is directed to a correlating a ECG measurement with GPS data comprising: an ECG measurement device comprising at least two detectors configured to detect a blood pulse from the blood circulation of a person and to be placed adjacent to a skin surface of the person, wherein the blood pulse is detected by the at least two detectors, and a strap configured to secure the apparatus to the person during use; a processor configured to verify that the blood pulse has been detected based on whether a first detection of the blood pulse associated with one of the at least two detectors occurs before a second detection of the blood pulse associated with another of the least two detectors, the processor being configured to determine the heart rate of the person on the basis of the detected blood pulse, wherein the processor is further configured to verify that the blood pulse has been detected based on whether the detections by the at least two detectors are separated by a predetermined time difference; a GPS sensor in communication with the apparatus. The ECG device can be configurable to be in communication with a communication network; a computer executable instruction that, when executed by a processor analyzes a received ECG data and a GPS data. Additionally, the computer executable instruction can be configured to analyze one or more of patient data and electronic device data. Historical user data and historical GPS data can also be accessible via a communication network.

Still another aspect of the disclosure is directed to an apparatus adapted to correlate a blood pressure measurement or ECG measurement with GPS data comprising: a measurement device wherein the measurement device is one of a blood pressure measurement device comprising a cuff for wrapping around a limb of a subject the cuff further having a an inflatable bladder formed integrally therein, wherein the cuff is substantially rectangular in shape having a first surface, a second surface, a first end, a second end, and two sides, and a securement mechanism, one or more tubes positioned within the cuff in communication with the inflatable bladder, an exhaust valve, and a housing connected to one of a first end and a second end of the cuff wherein the housing includes one or more of a controller, a memory, a pump, a power supply, and a motor or an ECG measurement device comprising at least two detectors configured to detect a blood pulse from the blood circulation of a person and to be placed adjacent to a skin surface of the person, wherein the blood pulse is detected by the at least two detectors, and a strap configured to secure the apparatus to the person during use, a processor configured to verify that the blood pulse has been detected based on whether a first detection of the blood pulse associated with one of the at least two detectors occurs before a second detection of the blood pulse associated with another of the least two detectors, the processor being configured to determine the heart rate of the person on the basis of the detected blood pulse, wherein the processor is further configured to verify that the blood pulse has been detected based on whether the detections by the at least two detectors are separated by a predetermined time difference, a GPS sensor in communication with the measurement device; and a transmitter for wirelessly transmitting measured data to a second device.

An aspect of the disclosure is directed to means for correlating a blood pressure measurement with GPS data. Suitable apparatuses comprise: a cuff means for wrapping around a limb of a subject the cuff means further having an inflatable bladder means formed integrally therein, wherein the cuff means is substantially rectangular in shape having a first surface, a second surface, a first end, a second end, and two sides, and a securement means; one or more tubular means positioned within the cuff means in communication with the inflatable bladder means; an exhaust valve means; a housing connected to one of a first end and a second end of the cuff means wherein the housing includes one or more of a controller, a memory, a pump, a power supply, and a motor; a GPS sensing means in communication with the apparatus; and a transmitter means for wirelessly transmitting blood pressure data to a second device. In some configurations, the blood pressure monitor device is configurable to be in communication with a communication network; and a computer executable instruction that, when executed by a processor analyzes a received blood pressure data and a GPS data. Additionally, the computer executable instructions can analyze one or more of patient data and electronic device data. In some configurations, the historical user data and historical GPS data is accessible via a communication network. One or more of an on-off button and a start-stop button can also be provided. Additionally, the device can comprise a pressure detector means, and/or a pulse detector means. Patient data and electronic device data can also be accessible via a communication network. Additionally, the blood pressure monitoring device is in wireless communication with one or more displays.

Another aspect of the disclosure is directed to a computing device comprising: a processor means configured to: receive a GPS location, a historic patient data, and physiological cardiac condition indication for a user wherein the physiologic cardiac condition is selected from heart rate, blood pressure, and ECG; at least one or more of analyze, monitor, evaluate, and provide a prediction for a user based on the GPS location of the user and the physiological cardiac condition indication for the user. The computing devices can further have a processor means that is configured to receive an input for stress level or activity level. Additionally, the processor means can be configured to at least one or more of analyze and evaluate the historical patient data. In at least some configurations, the processor is capable of generating and delivering a blood pressure event message to one or more of the user, and a healthcare provider. Additionally, the processor means can be associated with an electronic device and the electronic device is at least one of a blood pressure monitor and a mobile communication device. In still other configurations, the processor means is in communication with one or more of the electronic device, a remote server, and the blood pressure monitor within near field communication range.

Yet another aspect of the disclosure is directed to a correlating a ECG measurement with GPS data comprising: an ECG measurement sensing device means comprising at least two detection means configured to detect a blood pulse from the blood circulation of a person and to be placed adjacent to a skin surface of the person, wherein the blood pulse is detected by the at least two detection means, and a strap means configured to secure the apparatus to the person during use; a processor configured to verify that the blood pulse has been detected based on whether a first detection of the blood pulse associated with one of the at least two detectors occurs before a second detection of the blood pulse associated with another of the least two detectors, the processor being configured to determine the heart rate of the person on the basis of the detected blood pulse, wherein the processor is further configured to verify that the blood pulse has been detected based on whether the detections by the at least two detectors are separated by a predetermined time difference; a GPS sensor means in communication with the apparatus. The ECG device means can be configurable to be in communication with a communication network; a computer executable instruction that, when executed by a processor analyzes a received ECG data and a GPS data.

Additionally, the computer executable instruction can be configured to analyze one or more of patient data and electronic device data. Historical user data and historical GPS data can also be accessible via a communication network.

In some configurations, a biometric measurement device can include one or more light-emitting diodes (LED) and a photodiode or other optical sensor configured to detect blood composition or blood circulation of a person and to be placed adjacent to a skin surface of the person wherein the optical sensor measures the changing absorbance at one or more of the wavelengths, allowing it to determine an absorbance or reflectance due to the pulsing arterial blood alone, excluding venous blood, skin, bone, muscle, fat or other tissue. Additionally, processors can be configured to verify that the wavelength absorbance or reflectance. In some configurations, the apparatuses are configured to evaluate real-time biometric data, and real-time environmental and compare the information to historical biometric data and historical environmental data (such as data from GPS, barometers, accelerometers, and thermometers). Processors can also be configured to processor being configured to determine the rate of movement of blood within the blood vessels of the person or the concentration of hemoglobin and blood particles within the blood.

INCORPORATION BY REFERENCE

Any publications, patents, and patent applications mentioned in this specification are herein incorporated by reference to the same extent as if each individual publication, patent, or patent application was specifically and individually indicated to be incorporated by reference. See, for example, U.S. Pat. No. 4,776,344 A to Shirasaki et al. issued Oct. 11, 1988, for Electronic Blood Pressure Measuring Device;

U.S. Pat. No. 7,794,405 B2 to Karo et al. issued Sep. 14, 2010, for Cuff for Blood Pressure Monitor, and Blood Pressure Monitor Having the Same;

U.S. Pat. No. 8,509,882 B2 to Albert et al. issued Aug. 13, 2013, for Heart Monitoring System Usable with a Smart Phone or Computer;

U.S. Pat. No. 9,026,202 B2 to Albert issued May 5, 2015, for Cardiac Performance Monitoring System for Use with Mobile Communications Devices;

US 2013/0138000 A1 to Kinoshita et al. published May 30, 2013, for Blood Pressure Measurement Device;

US 2014/0371607 A1 to Peluso et al. published Dec. 18, 2014 for Devices and Methods for Measuring Blood Pressure; and US 2014/0378781 A1 to Peluso et al. published Dec. 25, 2014 for Methods and Systems for Acquiring Diagnostic Information.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
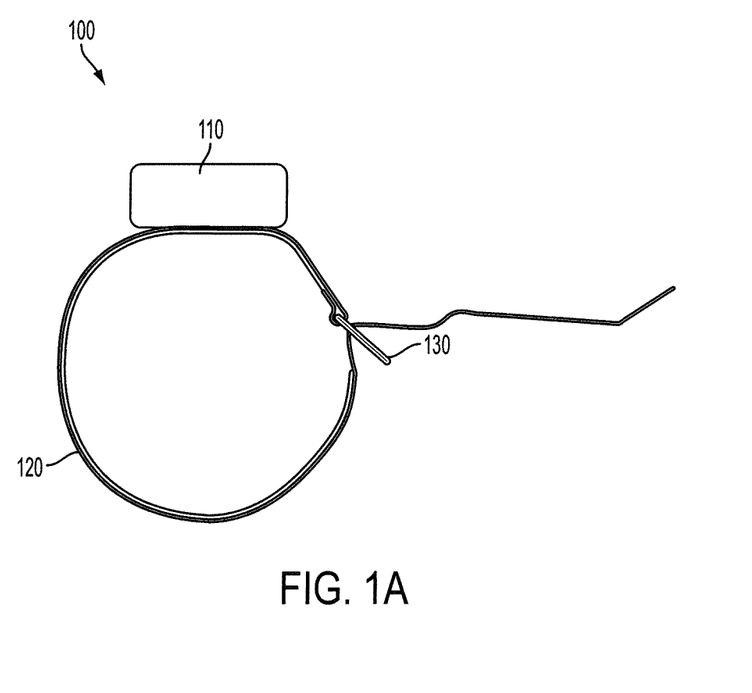
FIGS. 1A-H are views of an exemplar blood pressure measurement device suitable for use in the disclosed system.
Figure 1B:
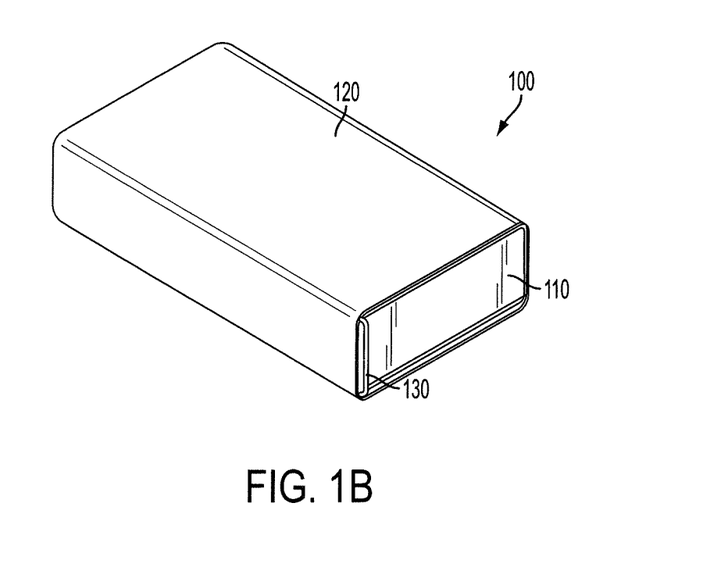
Figure 1C:
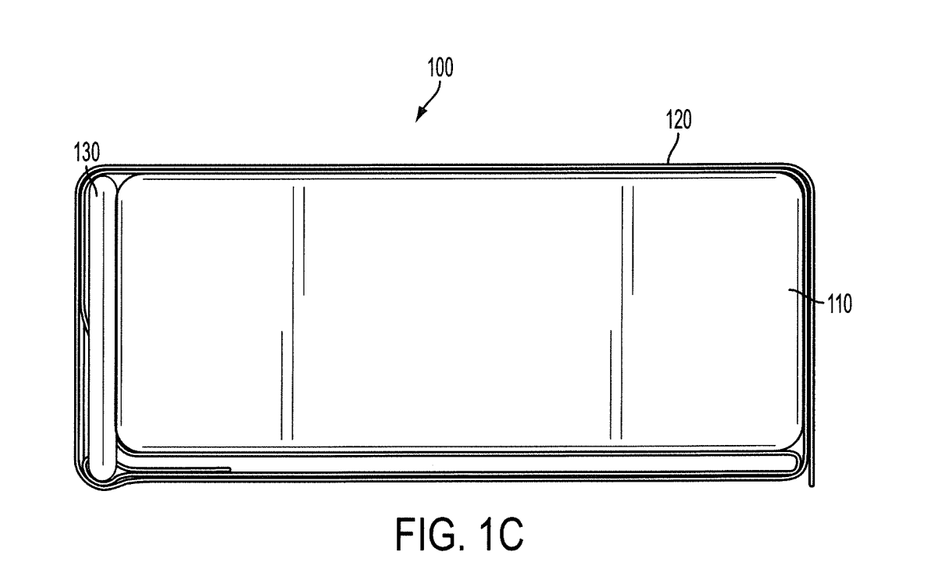
Figure 1D:
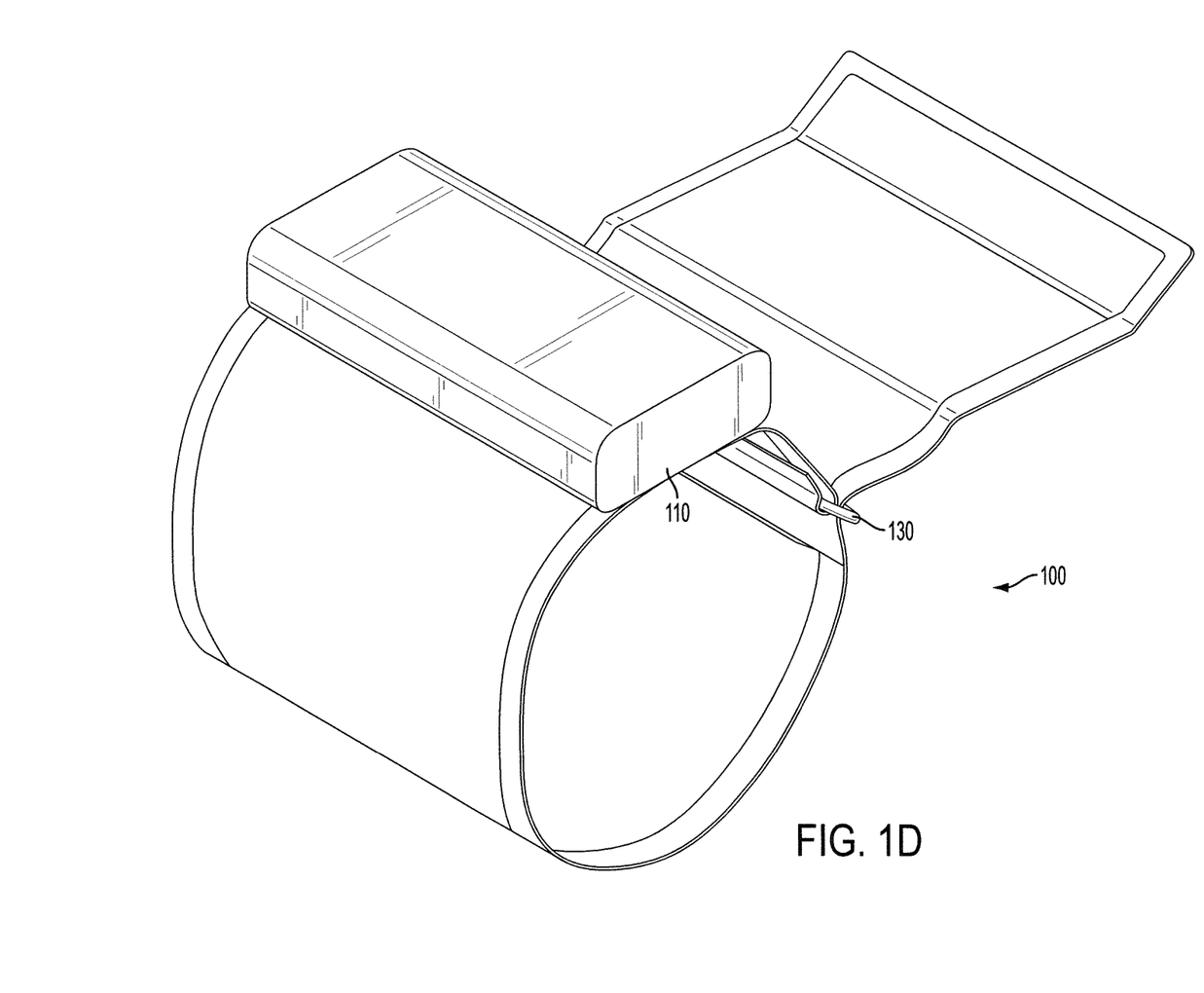
Figure 1E:
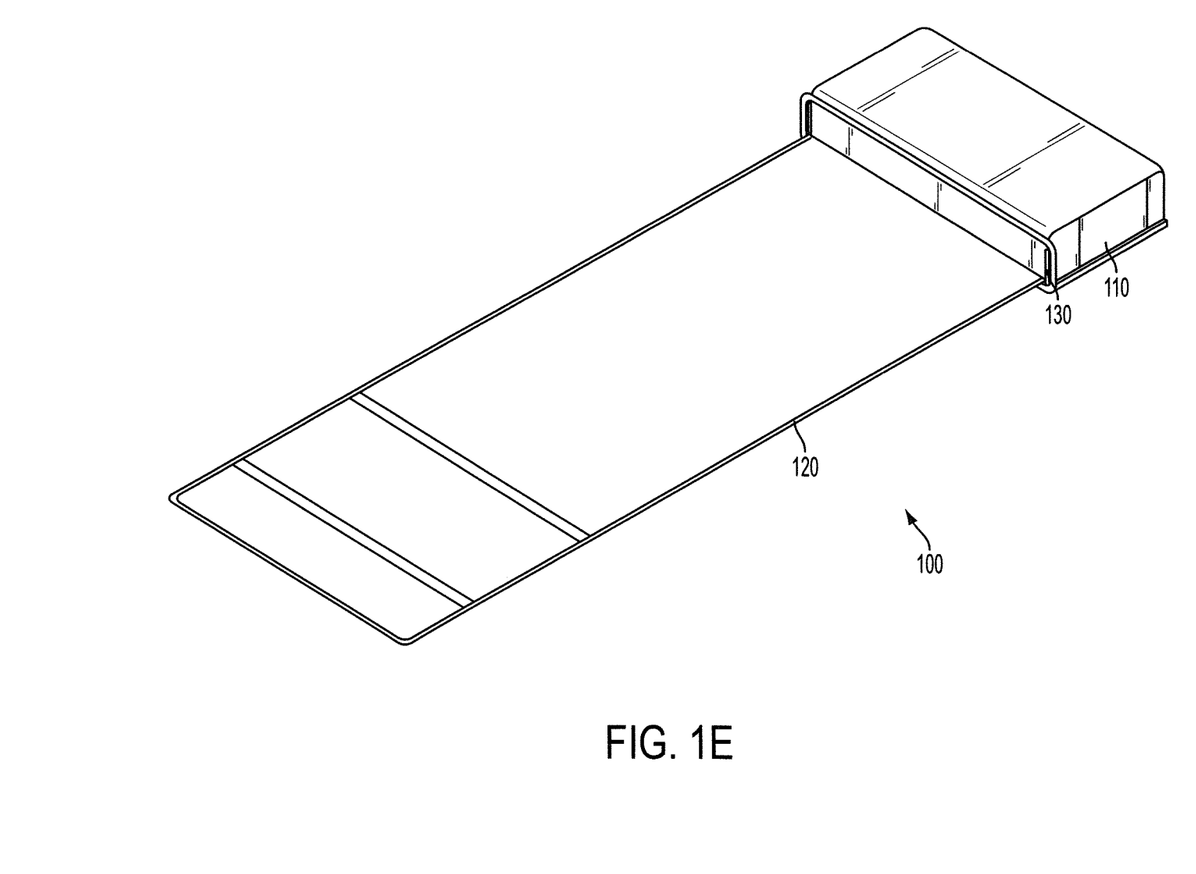
Figure 1F:
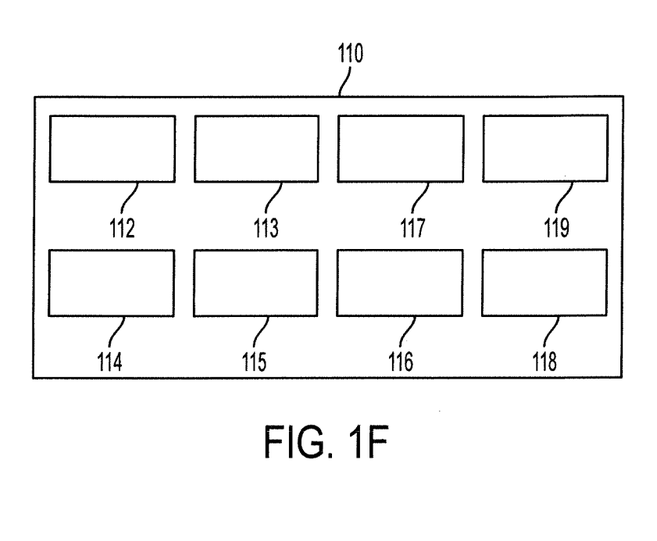
Figure 1G:
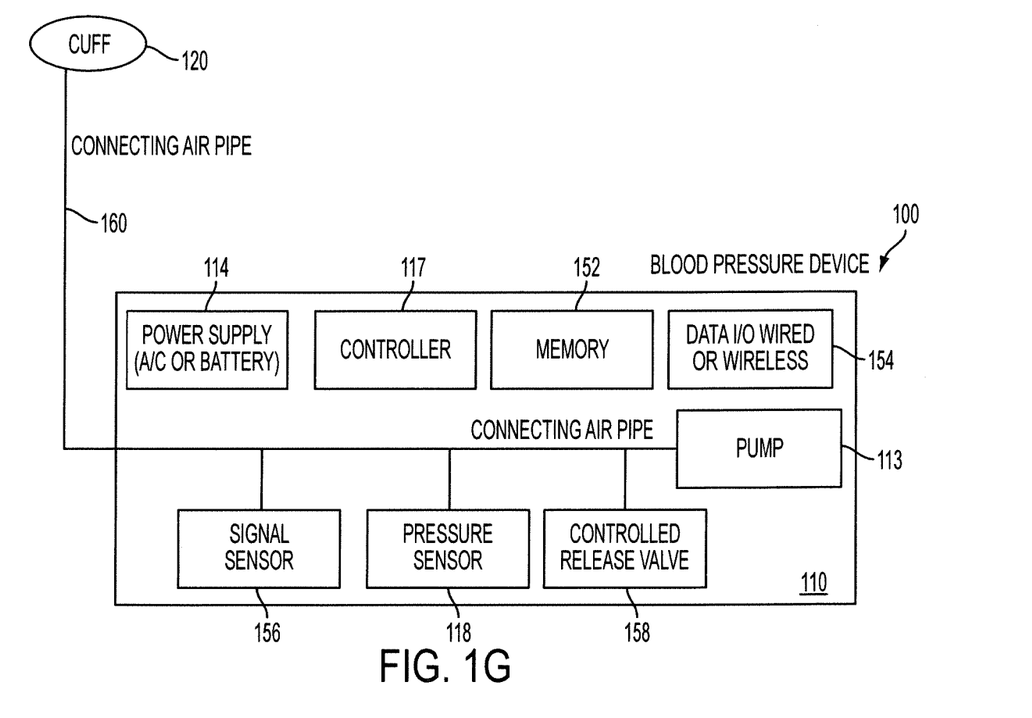

FIGS. 1A-H are views of an exemplar blood pressure measurement device 100 suitable for use in the disclosed systems and methods. The blood pressure measurement device 100 has a device body 110 which is configured to house the electronics required to measure blood pressure. The device body 110 has a three-dimensional rectangular shape (or cuboid shape) as illustrated in FIG. 1 with rounded edges in one plane (shown in FIGS. 1A-E). The housing 110 is secured one side of the housing to the cuff member 120 as best illustrated in FIG. 1A and FIG. 1G. The blood pressure measurement device 100 includes a cuff member 120 comprising, for example, a compression air bladder, a sub air bladder, and a pulse wave detection air bladder, pressure controller for pressurizing or depressurizing each air bladder, a pressure sensor which is capable of sensing an internal pressure of each air bladder, pulse wave signal extractor for extracting time-series data of a pulse wave signal superposed on a cuff internal pressure. A buckle or pulley 130 is provided through which the cuff member 120 can pass for securement around the arm of a user. When the cuff member 120 is unrolled from around the device body 110, the device can turn on; similarly when the cuff member 120 is secured around the device body 110 (e.g., for storage), the device can automatically turn off.

When the pressure controller in the device body 110 pressurizes or depressurizes each air bladder of the cuff member 120, a blood pressure value deriver capable of deriving a systolic blood pressure value and/or a diastolic blood pressure value based on a change in a feature amount of the pulse wave signal and a cuff internal pressure at a point of time of the change. Any wires, tubes or interface elements between the device body 110 and the cuff member 120 are not visible to the user.

To pressurize and depressurize the cuff member 120 which is adapted to be secured around (pulled tight), for example, a patient's arm, a pump is provided which has a connector which enables pressurizing/depressurizing connected to a compression air bladder of the cuff main body via a second tube and tube, to a pulse wave detection air bladder of the cuff main body via a first tube and fluid resistor, and to the sub air bladder of the cuff main body via a third tube and opening/closing valve. Also, a pressure sensor as a cuff pressure detector for obtaining a cuff pressure signal from the change in pressure of the pulse wave detection air bladder is connected to the pulse wave detection air bladder via the first tube. Furthermore, the third tube is connected to the sub air bladder.

The first, second, and third tubes, which are not visible to the user, are made of soft tubes. The third tube may be further connected to a damper device that increases the volume in proportion to the pressure and smooth the pressure. Other processes of pressurizing and depressurizing the cuff can be employed without departing from the scope of the disclosure.

As shown in FIG. 1F, the device body 110 is configurable to house the electronics which, for example, control the application of pressure to the cuff and analyze the resulting pressure data as well as transmitting the data 116 (e.g. via Bluetooth) to another device. For example, the pump 112 may be driven by a power supply 114 (e.g., battery) from a pump driver 113 connected to a motor 115, and supplies the external air into the pump through an opening, thereby performing pressurization. A controller 117 is provided which controls the operation of the device. The air bladders of the cuff can then be pressurized by supplying the pressurizing air to a tube or bladder. A rapid exhaust valve/constant-rate exhaust valve can be provided that has a structure in which the opening area can be changed by the magnitude of the electromagnetic force in order to achieve a depressurization rate of 2 to 4 mmHg/sec.

A pressure sensor 118, such as a cuff pressure detector, is configurable to receive a compression pressure signal from the compression air bladder, in which the pulse wave component is attenuated via the fluid resistor, and the pressure change of the pulse wave detection air bladder. A pressure measuring unit 119 for conversion into an analog electrical signal may be provided which is connected to the pressure sensor, and an analog-to-digital (A/D) converter is connected to the pressure measuring unit. The A/D converter can then output a digital signal as a cuff pressure signal to a controller 117.

The controller 117 is configurable to include a random access memory (RAM) for performing, for example, read and write of measurement data and analytical results, and a read only memory (ROM) for storing, as various control programs readable by the central controller, a pulse wave processor for detecting a pulse wave signal superposed on a cuff pressure signal, a cuff pressure controller for pressurizing and depressurizing the cuff (the compression air bladder, pulse wave detection air bladder, and sub air bladder), a blood pressure measuring unit for determining the blood pressure from the detected pulse wave change and compression cuff pressure signal. As would be evident to a person of skill in the art, the RAM can also function as a work area of programs to be processed by the controller 117.

The controller 117 is also in communication with a secondary electronic device 150 such as a mobile device which can act as a blood pressure display for displaying the final blood pressure value, and to drivers for performing the above-mentioned driving control operations. The power supply from a power supply unit, including batteries, is performed such that the central controller can perform each operation required for blood pressure measurement by supplying power to the corresponding unit in accordance with the operation of a switch.

As shown in FIG. 1G, a blood pressure measurement device 100 has a device body 110 which houses a power supply 114, a controller 117, a memory 152, a data i/o 154 which is wired or wireless, a signal sensor 156, a pressure sensor 118, a controlled release valve 158, and a pump 112 which is connected to the cuff member 120 by a connecting air pipe 160.

Figure 1H:
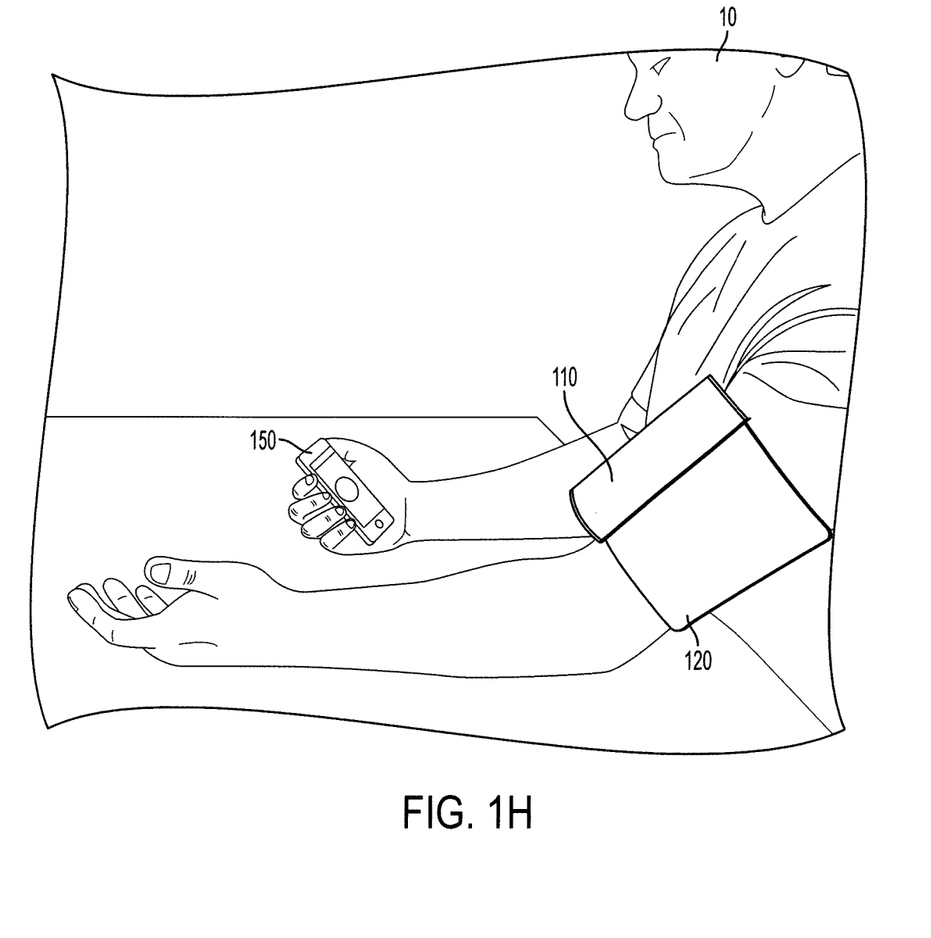

As shown in FIG. 1H, a user 10 has a blood pressure measurement device 100 comprising a cuff member 120 and a device body 110 secured about the arm of the user 10. The blood pressure measurement device 100 is in wireless communication with a secondary electronic device 150, such as a smart phone with a display.

Figure 2:
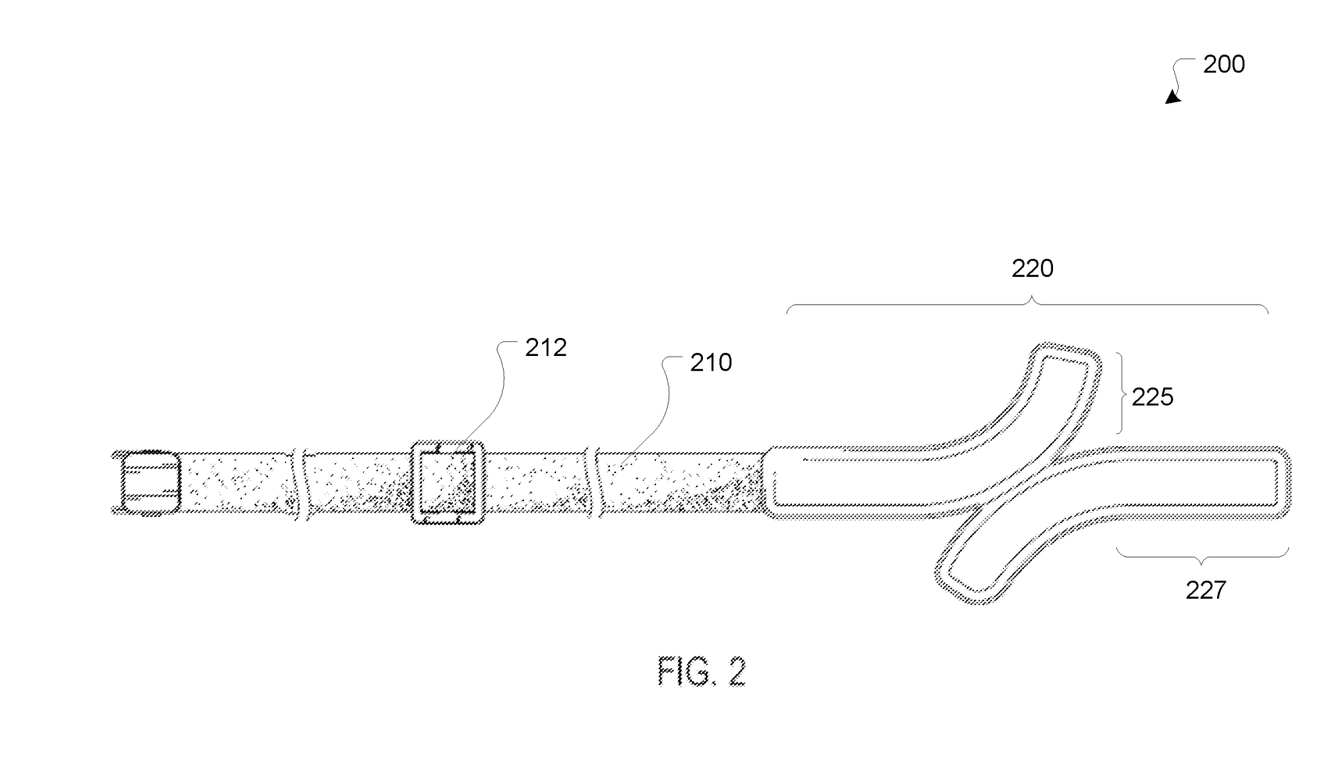
FIGS. 2-3 is an exemplar electrocardiogram monitor suitable for use in the disclosed system.
Figure 3:
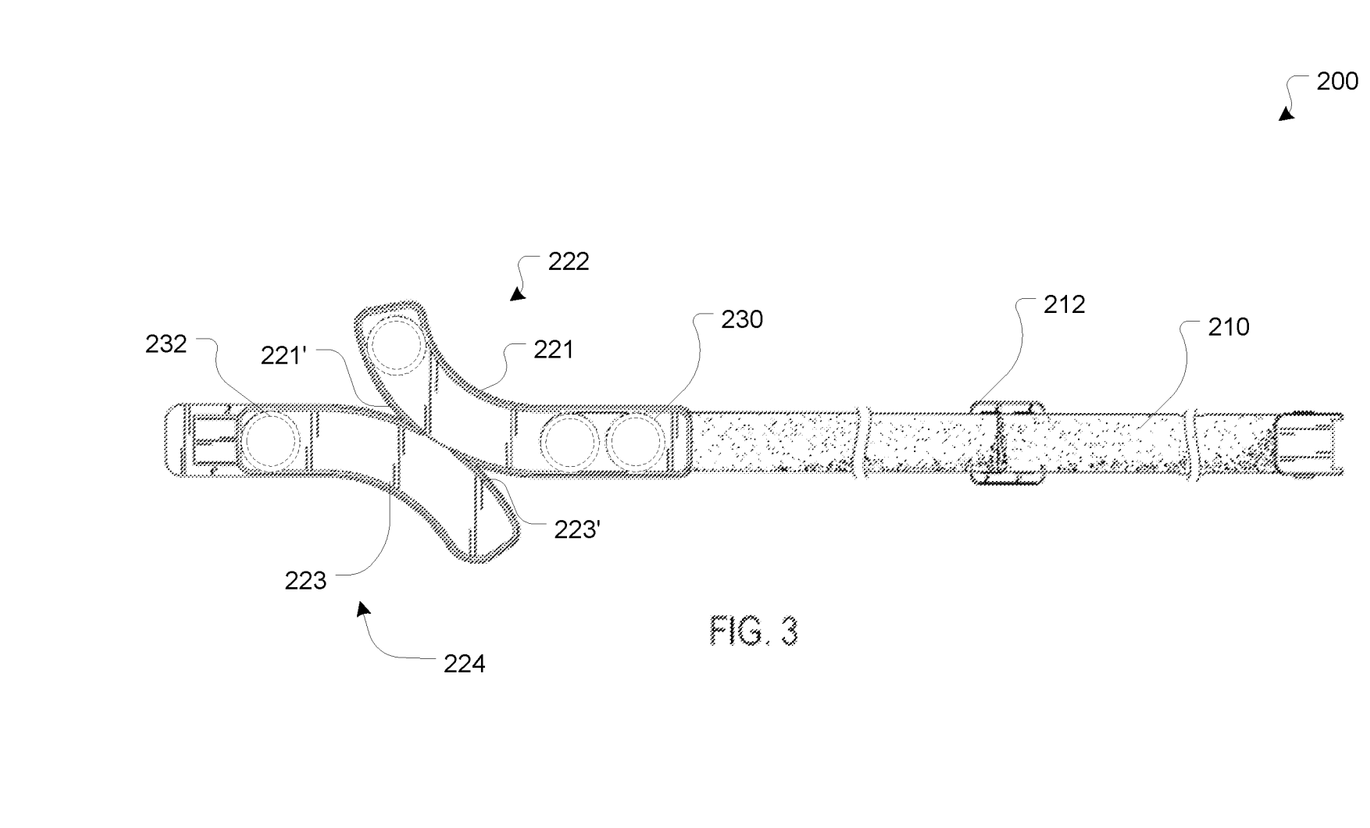

FIGS. 2-3 illustrate a wireless electrocardiogram monitor 200 from a first side and a second side. The wireless electrocardiogram monitor 200 has a strap 210 which is used to secure the sensor housing 220 to a user. The sensor housing 220 has a shape which is two curved L-shaped portions 222, 224. Each of the two curved L-shaped portions 222, 224 of the sensor housing 220 have an inner curve 221, 221' and an outer curve 223, 223', a short end 225 (or leg) and a long end 227 (or leg). The two curved L-shaped portions 222, 224 of the sensor housing 220 are positioned so that the inner curve 221 of the first curved L-shaped portion 222 is positioned away from the inner curve 221' of the second curved L-shaped portion 224. A buckle 212 is provided which allows the device to be adjustably secured during use. The sensor housing 220 has 4 sensors 230 positioned therein which come into contact with the skin surface of a user during use. Additionally, power source and a controller can be provided. The controller is configurable to receive information from the sensors and to wirelessly transmit the information to an electronic device. As evident from FIG. 3, the sensors 230 can be positioned so that not all sensors are positioned on the same line. For example, sensor 231 is positioned on a separate linear axis from the remaining sensors 230.

Figure 4:
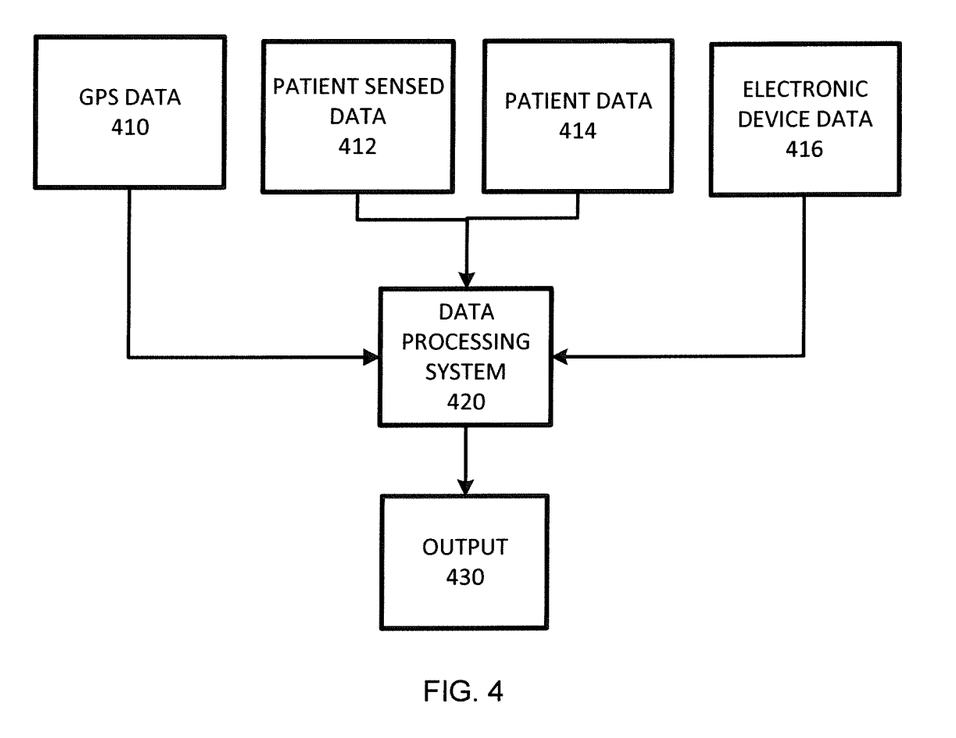
FIG. 4 is a block diagram that illustrates an interrelationship between data components in the devices and systems.
Figure 5:
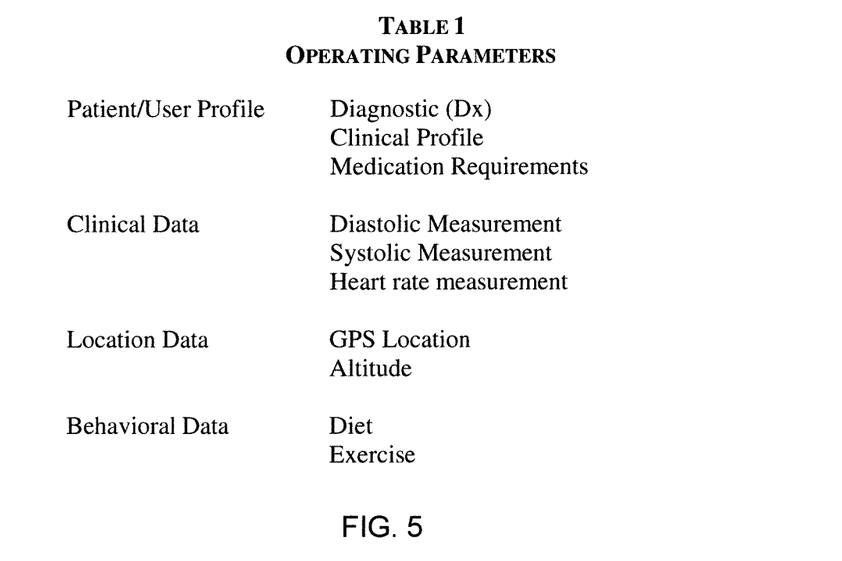
FIG. 5 is a table of operating parameters.

FIG. 4 illustrates an interrelationship between components of a suitable system according to the disclosure. Global positioning system (GPS) data 410 can be obtained from a sensor associated with the blood pressure measurement device 100, an electrocardiogram monitor 200 or from the secondary electronic device 150 in communication with the blood pressure measurement device 100 or electrocardiogram monitor 200. The patient (user) blood pressure and/or heart rate measurement data 412 is also provided by the blood pressure monitor. The information is then processed, using a data processing system 420 which is located either on a network or on the electronic device, to generate a blood pressure monitor output 430. The blood pressure and/or heart rate measurement data 412 can be correlated with other information such as time, date, and GPS data 416. The information can then be transmitted back to one or more remote location (such as a physician's office or other users). Additionally, patient data 414 can also be provided. Patient data can include, for example, perceived stress level, and/or activity level as well as other information relating to the patient, such as medications. Other sensors can also be provided to provide additional contextual data for use with the GPS data and/or the measurement device data (blood pressure measurement or electrocardiogram monitor). Other sensors, can include accelerometers (for movement detection), barometers, thermometers (for both environmental and body temperature measurement), UV exposure, noise, galvanic skin response, body posture, and skin hydration.

The system is also configurable to analyze GPS information, which can include altitude information, for a particular patient or user based on one or more of the following: the patient's prior history under similar conditions, or a similar history under similar conditions previously experienced.

Other aspects include one or more networked devices. The networked devices comprise: a memory; a processor; a communicator; a display; and an apparatus for detecting blood pressure as discussed herein.

Communication systems are configurable to have at least one of an API engine connected to at least one of the electronic device to create a message about blood pressure data or ECG data and transmit the message over an API integrated network to a recipient having a predetermined recipient user name, a messaging engine connected to the system to create a message about the blood pressure data or ECG data and transmit such message over a network to a recipient device having a predetermined blood pressure data or ECG data recipient IP address, telephone number, or other messaging engine unique identifier, and an email engine connected to the system to create an email message about the blood pressure data or ECG data and transmit the email message over the network to a recipient email. As would be understood by a person of skill in the art, an application programming interface (API) is a set of routines, protocols, and tools for the facilitation of the exchange of data between two or more elements of a data systems or between two or more data systems A storing module can also be provided on the server computer system for storing the blood pressure data or ECG data on the system for measuring the characteristic of the blood pressure server database. Moreover, the system is connectable to a server computer system over at least one of a mobile phone network and an Internet network, and a browser on the recipient electronic device which can be used to retrieve an interface on the server computer system. Additionally, a plurality of email addresses are held in a system database and fewer than all the email addresses are individually selectable from the computer system, the email message being transmitted to at least one data recipient email having at least one selected email address. In some instances the system is connectable to the server computer system over the Internet, and a browser on the electronic device to retrieve an interface on the server computer system. A plurality of user names are held in the system database and fewer than all the user names are individually selectable from the computer system, enabling a message to be transmitted to at least one blood pressure data or ECG data recipient user name via an API.

Other aspects include one or more networked apparatuses. The networked apparatuses comprise: a memory; a processor; a communicator; a display; and an apparatus for receiving user input rates as described herein.

At the time of measurement of a cardiac data, a global positioning system ("GPS system") is, if not already active, activated, and the cardiac data measurement is performed using a blood pressure monitor, at about the same time, geolocation data or other contextual data on the measurement are collected. In at least some embodiments, the measurement data and GPS data are transmitted and stored in a central location (e.g., a cloud server). In an alternative configuration, the data is stored locally, e.g. either on the measurement device or on a device in wired or wireless communication with the measurement device. As will be appreciated by those skilled in the art, the electronics and software for the GPS system can be resident on a measurement device or on a device in wired or wireless communication with a measurement device. For example, a blood pressure monitor in wired or wireless communication with a mobile device.

The system is configurable such that the blood pressure measurement data and corresponding GPS data associated with the measurement data can be accessed by one or more users (e.g. the patient, or an authorized family member, or a healthcare provider) on request.

The systems and methods are configurable to automatically recognize recurring locations or other recurring contextual information. As will be appreciated by those skilled in the art, the system can be configurable such that a cluster can occur when a user takes a measurement within proximity of a prior measurement. Thus, clustering of data can occur when measurements are taken within, for example, 100 feet of certain locations, like home, office, school, and so on. Similarly, clustering of data can occur where the GPS measurement is different than a prior GPS measurement but the altitude at which the GPS measurement is taken is between 500 and 100 meters above sea level, or between 1000 and 1500 meters above sea level, between 1500 and 2000 meters above sea level, of another measurement, and so on. Furthermore, as will be appreciated by those skilled in the art, the system can be configurable such that the system is capable of rejecting and/or otherwise notifying a user about a measurement performed outside of the sensor's effective operating range.

Systems are configurable to incorporate a variety of operating parameters such as those provided for in FIG. 3, including patient/user profile information (diagnostic data, clinical profile, medical requirements), clinical data (diagnostic measurement, systolic measurement), location data (GPS location, altitude), and/or behavioral data (diet, exercise). As will be appreciated by those skilled in the art, the behavioral data regarding diet, for example, can provide additional information pertinent to measuring blood pressure, such as sodium intake or daily level of general physical activity.

EXAMPLES

A. User Measures Blood Pressure at Two Different GPS Locations.

The system is configured to recognize a location and stores a value of a biometric reading, such as a blood pressure or ECG reading, along with locational data and/or time data. Sometime later, the user is at second location and takes a second biometric measurement. The system records the new location and the value of the biometric reading and tracks that the two measurements are taken in different locations and the user was exposed to different conditions.

As data is collected, the system is configurable to identify trends such as detecting that a certain health issue is more likely to manifest itself under certain conditions (trigger conditions) that are, for example, present in one or more locations, and not in others. With this trend information, the user can then act to avoid or mitigate such triggering conditions, and thus improve overall health management or health condition management.

B. User Measures Blood Pressure at a Similar Altitude

The system recognizes the location of a first biometric reading being taken at a first altitude and stores the value of the reading. Sometime later, the user is at a second location having a same or similar altitude. The system records the new location and the value of the second biometric reading and tracks that the two measurements are taken in different locations but similar altitudes. The system might allow detecting that a certain health issue is more likely to manifest itself under certain conditions (such as altitude) that are, for example, present in a one or more locations, and not in others. The user can then act to avoid or mitigate such trigger conditions, and thus improve overall health management or health condition management.

The systems and methods according to aspects of the disclosed subject matter may utilize a variety of computer systems, communications devices, networks and/or digital/logic devices for operation. Each may in turn utilize a suitable computing device, which can be manufactured with, loaded with and/or fetch from some storage device, and then execute, instructions that cause the computing device to perform a method according to aspects of the disclosed subject matter. A computing device can include without limitation a mobile user device such as a smart watch, a mobile phone, a smart phone and a cellular phone, a personal digital assistant ("PDA"), such as a Android® or iPhone®, a tablet, a laptop and the like.

In at least some configurations, a user can execute a browser application over a network, such as the Internet, to view and interact with digital content, such as screen displays. Access could be over or partially over other forms of computing and/or communications networks. A user may access a web-browser, e.g., to provide access to applications and data and other content located on a website or a webpage of a website.

A suitable computing device may include a processor to perform logic and other computing operations, e.g., a stand-alone central processing unit ("CPU"), or hard wired logic as in a microcontroller, or a combination of both, and may execute instructions according to its operating system and the instructions to perform the steps of the method. The computing device of a user may be part of a network of computing devices and the methods of the disclosed subject matter may be performed by different computing devices, perhaps in different physical locations, cooperating or otherwise interacting to perform a disclosed method. For example, a portable computing device of a user may run an app alone or in conjunction with a remote computing device, such as a server on the Internet. As will be appreciated by those skilled in the art, "computing device" includes any and all of the above discussed logic circuitry, communications devices and digital processing capabilities or combinations of these.

Certain embodiments of the disclosed subject matter may be described for illustrative purposes as steps of a method which may be executed on a computing device executing software, and illustrated, by way of example only, as a block diagram of a process flow. Such may also be considered as a software flow chart. Such block diagrams and like operational illustrations of a method performed or the operation of a computing device and any combination of blocks in a block diagram, can illustrate, as examples, software program code/instructions that can be provided to the computing device or at least abbreviated statements of the functionalities and operations performed by the computing device in executing the instructions. Some possible alternate implementation may involve the function, functionalities and operations noted in the blocks of a block diagram occurring out of the order noted in the block diagram, including occurring simultaneously or nearly so, or in another order or not occurring at all. Aspects of the disclosed subject matter may be implemented in parallel or seriatim in hardware, firmware, software or any combination(s) of these, co-located or remotely located, at least in part, from each other, e.g., in arrays or networks of computing devices, over interconnected networks, including the Internet, and the like.

A machine readable medium is also disclosed storing instructions that, when executed by a computing device, can cause the computing device to perform a method, according to the disclosure contained herein.

The instructions may be stored on a suitable "machine readable medium" within a computing device or in communication with or otherwise accessible to the computing device. As used in the present application a machine readable medium includes a tangible storage device and the instructions are stored in a non-transitory way. At the same time, during operation, the instructions may at times be transitory, e.g., in transit from a remote storage device to a computing device over a communication link. However, when the machine readable medium is tangible and non-transitory, the instructions will be stored, for at least some period of time, in a memory storage device, such as a random access memory (RAM), a read only memory (ROM), a magnetic or optical disc storage device, or the like, arrays and/or combinations of which may form a local cache memory, e.g., residing on a processor integrated circuit, a local main memory, e.g., housed within an enclosure for a processor of a computing device, a local electronic or disc hard drive, a remote storage location connected to a local server or a remote server access over a network, or the like. When so stored, the software can constitute a "machine readable medium," that is both tangible and stores the instructions in a non-transitory form. At a minimum, therefore, the machine readable medium storing instructions for execution on an associated computing device will be "tangible" and "non-transitory" at the time of execution of instructions by a processor of a computing device and when the instructions are being stored for subsequent access by a computing device.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system adapted to provide contextualized biometric data from a plurality of sources comprising:
   a blood pressure monitor comprising
      a cuff operable to securely wrap around a limb of a subject when the blood pressure monitor is in a deployed condition, the cuff having an inflatable bladder formed integrally therein, wherein the cuff is substantially rectangular in shape having a first surface for engaging the limb of the subject in the deployed condition, a second surface, a first end, a second end, and two sides, a cuff length greater than a cuff width, a securement mechanism for securing the cuff in the deployed configuration;
      one or more tubes positioned within the cuff in communication with the inflatable bladder;
      an exhaust valve;
      a three-dimensional rectangular housing having rounded edges in one planar dimension, wherein the housing includes one or more of a controller, a memory, a pump, a power supply and a motor, and further wherein a portion of the second surface of the cuff is secured to an exterior surface of the housing on a first housing side and the second surface of the cuff faces the housing when the blood pressure monitor is in an undeployed condition;
      a transmitter for wirelessly transmitting blood pressure data to a second device, and
   a heart rate monitor comprising
      a sensor housing having
         a first curved L-shaped housing portion having a first leg and a second leg longer than the first leg, a first side with a first inner curve and second side opposite the first side with a first outer curve, and a first sensor in the first leg of the curved L-shaped housing portion, and a second sensor and a third sensor in the second leg of the first curved L-shaped housing portion,
         a second curved L-shaped housing portion having a first leg and a second leg longer than the first leg, a first side with a second inner curve and a second side different than the first side with a second outer curve, and a fourth sensor in the second leg of the second curved L-shaped housing portion, wherein the first inner curve of the first L-shaped housing portion and the first inner curve of the second L-shaped housing portion are positioned on opposite sides of the sensor housing, the first outer curve of the first L-shaped housing portion and the first outer curve of the second L-shaped housing portion are adjacent one another, further wherein, the second sensor and the third sensor are positioned on a first axis with the fourth sensor, and the first sensor is positioned on a second axis perpendicular to the first axis, wherein each sensor is intersected by only one axis of the first axis and the second axis, and a strap configured to secure the heart rate monitor to a subject during use and a heart rate transmitter for wirelessly transmitting heart rate data;

a contextual data gathering sensor configured to gather contextual data concurrently with the biometric data gathered from the blood pressure monitor and the heart rate monitor; and a secondary electronic device in wireless communication with the at least one biometric data gathering device wherein the secondary electronic device receives measurement data from the at least one biometric data gathering device and provides a display of a biometric data from the at least one biometric data gathering device.

2. The system of claim 1 wherein the blood pressure monitor and heart rate monitor are configurable to be in communication with a communication network having a processor; and a computer executable instruction that, when executed by the processor analyzes a received biometric data and contextual data.

3. The apparatus of claim 2 wherein patient data and electronic device data is accessible via the communication network.

4. The system of claim 1 wherein the computer executable instruction analyzes one or more of biometric data and contextual data.

5. The system of claim 1 wherein historical biometric data and historical contextual data is accessible via a communication network.

6. The system of claim 1 further comprising one or more of an accelerometer, a barometer, a thermometer, a UV sensor, a microphone, a galvanic skin response sensor, a body posture sensor, and skin hydration sensor in communication with the apparatus.

7. The system of claim 1 further comprising an atmospheric pressure detector.

8. The system of claim 1 further comprising a pulse detector.

9. The system of claim 1 wherein the blood pressure monitor and heart rate monitor are in wireless communication with one or more displays.

10. A method of evaluating contextualized biometric data comprising:

deploying a blood pressure monitor comprising
a cuff operable to securely wrap around a limb of a subject when the blood pressure monitor is in a deployed condition, the cuff having an inflatable bladder formed integrally therein, wherein the cuff is substantially rectangular in shape having a first surface for engaging the limb of the subject in the deployed condition, a second surface, a first end, a second end, and two sides, a cuff length greater than a cuff width, a securement mechanism for securing the cuff in the deployed configuration;

one or more tubes positioned within the cuff in communication with the inflatable bladder;

an exhaust valve;

a three-dimensional rectangular housing having rounded edges in one planar dimension, wherein the housing includes one or more of a controller, a memory, a pump, a power supply and a motor, and further wherein a portion of the second surface of the cuff is secured to an exterior surface of the housing on a first housing side and the second surface of the cuff faces the housing when the blood pressure monitor is in an undeployed condition;

a transmitter for wirelessly transmitting blood pressure data to a second device, and deploying a heart rate monitor comprising
a sensor housing having
a first curved L-shaped housing portion having a first leg and a second leg longer than the first leg, a first side with a first inner curve and second side opposite the first side with a first outer curve, and a first sensor in the first leg of the curved L-shaped housing portion, and a second sensor and a third sensor in the second leg of the first curved L-shaped housing portion, a second curved L-shaped housing portion having a first leg and a second leg longer than the first leg, a first side with a second inner curve and a second side different than the first side with a second outer curve, and a fourth sensor in the second leg of the second curved L-shaped housing portion, wherein the first inner curve of the first L-shaped housing portion and the first inner curve of the second L-shaped housing portion are positioned on opposite sides of the sensor housing, the first outer curve of the first L-shaped housing portion and the first outer curve of the second L-shaped housing portion are adjacent one another, further wherein, the second sensor and the third sensor are positioned on a first axis with the fourth sensor, and the first sensor is positioned on a second axis perpendicular to the first axis, wherein each sensor is intersected by only one axis of the first axis and second axis, and a strap configured to secure the heart rate monitor to a subject during use and a heart rate transmitter for wirelessly transmitting heart rate data; and connecting the one or more biometric data devices wirelessly to a secondary electronic device having a display;

collecting biometric data from the blood pressure monitor and the heart rate monitor;

collecting non-biometric contextual data from a contextual data gathering sensor configured to gather contextual data concurrently with the biometric data; and correlating the collected blood pressure monitoring data and heart rate monitoring data with the collected contextual data to generate a contextual biometric data.

11. The method of claim 10 further comprising the step of transmitting the contextual biometric data via a network.

* * * * *